US007517950B2

(12) United States Patent
Sugiyama et al.

(10) Patent No.: US 7,517,950 B2
(45) Date of Patent: Apr. 14, 2009

(54) TUMOR ANTIGEN BASED ON PRODUCTS OF THE TUMOR SUPPRESSOR GENE WT1

(75) Inventors: Haruo Sugiyama, Mino (JP); Yoshihiro Oka, Tondabayashi (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 157 days.

(21) Appl. No.: 11/322,245

(22) Filed: Jan. 3, 2006

(65) Prior Publication Data
US 2006/0093615 A1    May 4, 2006

Related U.S. Application Data

(63) Continuation of application No. 09/744,815, filed as application No. PCT/JP99/04130 on Jul. 30, 1999, now Pat. No. 7,030,212.

(30) Foreign Application Priority Data
Jul. 31, 1998    (JP)    ................. 10-218093

(51) Int. Cl.
   C07K 14/00    (2006.01)
   A61K 38/00    (2006.01)
(52) U.S. Cl. .......................... 530/300; 514/2
(58) Field of Classification Search ................ None
   See application file for complete search history.

(56) References Cited

U.S. PATENT DOCUMENTS

| | | | |
|---|---|---|---|
| 5,622,835 | A | 4/1997 | Herlyn et al. |
| 5,726,288 | A | 3/1998 | Call et al. |
| 5,840,839 | A | 11/1998 | Wang et al. |
| 6,034,235 | A | 3/2000 | Sugiyama et al. |
| 6,207,880 | B1 | 3/2001 | Kossmann et al. |
| 2003/0039635 | A1 | 2/2003 | Gaiger et al. |
| 2003/0072767 | A1 | 4/2003 | Gaiger et al. |
| 2003/0082196 | A1 | 5/2003 | Gaiger et al. |
| 2003/0095971 | A1 | 5/2003 | Gaiger et al. |
| 2003/0198622 | A1 | 10/2003 | Gaiger et al. |
| 2003/0215458 | A1 | 11/2003 | Gaiger et al. |
| 2003/0235557 | A1 | 12/2003 | Gaiger et al. |
| 2004/0018204 | A1 | 1/2004 | Gaiger et al. |
| 2004/0097703 | A1 | 5/2004 | Sugiyama |
| 2004/0126362 | A1 | 7/2004 | Gaiger et al. |
| 2004/0247609 | A1 | 12/2004 | Sugiyama |
| 2005/0002951 | A1 | 1/2005 | Sugiyama et al. |
| 2005/0266014 | A1 | 12/2005 | Sugiyama et al. |

FOREIGN PATENT DOCUMENTS

| | | |
|---|---|---|
| EP | 1 004 319 | 7/1998 |
| EP | 1 074 267 | 7/2000 |
| EP | 1 103 564 | 5/2001 |
| JP | 61-22018 | 1/1986 |
| JP | 09-104629 | 4/1997 |
| JP | 2001-89389 | 4/2001 |
| WO | WO 91/07509 | 5/1991 |
| WO | WO 95/16464 | 6/1995 |
| WO | WO 95/29995 | 11/1995 |
| WO | WO 96/02555 | 2/1996 |
| WO | WO 96/38176 | 12/1996 |
| WO | WO 99/44634 | 9/1999 |
| WO | WO 00/06602 | 2/2000 |
| WO | WO 00/18795 | 4/2000 |
| WO | WO 00/26249 | 5/2000 |
| WO | WO 00/41463 | 7/2000 |
| WO | WO 00/44349 | 8/2000 |
| WO | WO 01/62920 | 8/2001 |
| WO | WO 02/079253 | 10/2002 |
| WO | WO 03/106682 | 12/2003 |

OTHER PUBLICATIONS

Gaiger et aL (Blood, vol. 96, No. 4, Aug. 2000, pp. 1480-1489.*
F. J. Rauscher, III, et al., "Characterization of Monoclonal Antibodies Dirrected to the Amino-Terminus of the WT1, Wilms' Tumor Suppressor Protein", Hybridoma, vol. 17, No. 2, Apr. 1998, pp. 191-198.
H. G. Rammensee, et al., "Peptides Naturally Presented by MHC Class I Molecules", Ann. Rev. Immunol, 1993, pp. 213-244.
U.S. Appl. No. 09/744,815, filed Jan. 30, 2001, Sugiyama et al.
U.S. Appl. No. 10/517,600, filed Dec. 13, 2004, Sugiyama et al.
U.S. Appl. No. 10/527,692, filed Mar. 11, 2005, Sugiyama.
U.S. Appl. No. 10/528,360, filed Mar. 18, 2005, Sugiyama et al.
U.S. Appl. No. 11/196,452, filed Aug. 4, 2005, Sugiyama et al.
U.S. Appl. No. 10/541,821, filed Jul. 11, 2005, Sugiyama et al.
U.S. Appl. No. 10/562,486, filed Dec. 27, 2005, Sugiyama.
U.S. Appl. No. 11/322,245, filed Jan. 3, 2006, Sugiyama et al.
A. J. Buckler, et al., "Isolation, Characterization, and Expression of the Murine Wilms' Tumor Gene (WT1) During Kidney Devleopment", Molecular and Cellular Biology, vol. 11, No. 3, 1991, pp. 1707-1712.
D.M. Pardoll, "New Strategie for Enhancing the Immunogenicity of Tumors", Current Opinion in Immunology, vol. 5, No. 5, 1993, pp. 719-725.
C.M. Melief, et al., "Potential Immunogenicity of Oncogenea and Tumor Suppressor Gene Products", Current Opinion in Immunology, vol. 5, No. 5, 1993, pp. 709-713.
H.G. Rammensee, et al., "MHC Ligands and Peptide Motifs: First Listing", Immunogenetics, vol. 41, No. 4, 1995, pp. 178-228.
B. Palermo, et al., "Cytotoxic T-lymphocyte responses in melanoma through in vitro stimulation with the Melan-A peptide analogue A27L: a Qualitative Analysis", Melanoma Research, 2002, 12, pp. 491-498.
L. Gao, et al, "Selective Elimation of Leukemic CD34+ Progenitor Cells by Cytotoxic T Lymphocytes Specific for WT1", Blood, Apr. 1, 2000, vol. 95, No. 7, pp. 2198-2203.
N. Renkvist, et al., "A Listing of Human Tumor Antigens Recognized by T Cells", Cancer Immunol. Immunother, 2001, 50: pp. 3-15.

(Continued)

Primary Examiner—Christopher H Yaen
(74) Attorney, Agent, or Firm—Oblon, Spivak, McClelland, Maier & Neustadt, P.C.

(57) ABSTRACT

A tumor antigen that comprises, as an active ingredient, a product of the Wilms' tumor suppressor gene WT1 or a peptide composed of 7-30 contiguous amino acids containing an anchor amino acid for binding to major histocompatibility complex (MHC) class I in said amino acid sequence, and a vaccine comprising said antigen.

9 Claims, 16 Drawing Sheets

OTHER PUBLICATIONS

M. Gessler, et al., "Homozygous Deletion in Wilms Tumours of a Zinc-Finger Gene Identified by Chromosome", Nature, vol. 343, Feb. 22, 1990, pp. 774-778.

A. Tsuboi, et al., "Cytotoxic T-Lymphocyte Responses Elicited to Wilms' Tumor Gene WT1 Product by DNA Vaccination", Journal of Clinical Immunology, vol. 20, No. 3, 2000, pp. 195-202.

A. Gaiger, et al., "Immunity of WT1 in the Animal Model and in Patients with Acute Myeloid Leukemia", Aug. 15, 2000, vol. 96, No. 4, pp. 1480-1489.

W. Barclay, et al., "Effects of Oil-Treated Mycobacterial Cell Walls of the Organs of Mice", Journal of Bacteriology, No. 1967, pp. 1736-1745.

M. Yamawaki, et al., "Antitumor Activity of Squalene-Treated Cell-Wall Skeleton of Nocardia Rubra in Mice", Gann, vol. 69, No. 5, pp. 619-626, 1978.

Y. Oka, et al., XP-000884935, vol. 51, No. 2, Feb. 1, 2000, "Human Cytotoxic T-Lymphocyte Responses Specific for Peptides of the Wild-Type Wilms' Tumor Gene (WT1) Product".

M. Yasukawa, et al., "HLA Class I-Restricted Lysis of Leukemia Cells by a CD8+ Cytotoxic T-Lymphocyte Clone Directed Against WT1 Peptide", Blood, Nov. 15, 1998, vol. 92, No. 10, Part 1, Suppl. 1: Abstract p. 2541.

Gura, "Systems for Identifying New Drugs Are Often Faulty", Science, vol. 278, 1997, pp. 1041-1042.

M. Bellone, et al., "Cancer Immunotherapy: Synthetic and Natural Peptides in the Balance", Immunology Today, vol. 20, No. 10, Oct. 1999, pp. 457-461.

A. Gaiger, et al., "Immunity to WT1 in the Animal Model and in Patients with Acute Myeloid Leukemia", Blood, vol. 96, No. 4, Aug. 15, 2000, pp. 1480-1489.

A. Gaiger, et al., "WT1: A New Leukemia and Cancer Antigen", Proceeding of the American Association for Cancer Research Annual Meeting, vol. 40, Mar. 1999, p. 424.

Patent Family Information of Attached Reference WO 00/18795, no date.

Patent Family Information of Attached Reference WO 00/26249, no date.

I. Roitt, et al., Immunology, 4th Ed., 1996, Mosby, pp. 7.9-7.11.

Y. Oka, et al., "Induction of WT1 (Wilms' Tumor Gene)-specific Cytotoxic T Lymphocytes by WT1 Peptide Vaccine and the Resultant Cancer Regression", 2004, vol. 101, No. 38, pp. 13885-13890.

I. Higashi, Biomedicine & Therapeutics, 1988, vol. 20, No. 1, pp. 21-26, "BRM to shite no Saikin Kintai Seibun".

B. Zbar, et al., "Tumor Suppression by Cell Walls of Mycobacterium Bovis Attached to Oil Droplets[1]", Journal of the National Cancer Institute, vol. 48, No. 3, Mar. 1972, pp. 831-835.

M. Singh, et al., "Advances in Vaccine Adjuvants", Nature Biotechnology, vol. 17, Nov. 17, 1999, pp. 1075-1081.

F. Nestle, et al., Vaccination of Melanoma Patients with Peptide- or Tumor Lysate-Pulsed Dendritic Cells, Nature Medicine, vol. 4, No. 3, Mar. 1998, pp. 328-332.

L. Chedid, et al., Protective Effect of Delipidated Mycobacterial Cells and Purified Cell Walls Against Ehrlich Carcinoma and a Syngeneic Lymphoid Leukemia in Mice[1], Cancer Research, 33, Sep. 1973, pp. 2187-2195.

C. Melief, et al., "T-Cell Immunotherapy of Tumors by Adoptive Transfer of Cytotoxic T Lymphocytes and by Vaccination wit Minimal Essential Epitopes", Immunological Reviews, 1995, No. 146, pp. 167-177.

Y. Oka, et al., Hematology Frontier, 2000, vol. 10, No. 8, pp. 1017-1023, "3. Men'eki Ryoho 2) WT1 o Hyotekki to shita Hakketsubyo ni Taisuru Tokuiteki Men'eki Ryoho".

E. Ribi, et al., "Factors Influencing Protection Against Experimental Tuberculosis in Mice by Heat-Stable Cell Wall Vaccines", Journal of Bacteriology, Oct. 1966, vol. 92, No. 4, pp. 869-879.

H. Sugiyama, "Wilms' Tumor Gene WT1: Its Oncogenic Function and Clinical Application", International Journal of Hematology, vol. 73, 2001, pp. 177-187.

R. Lin, et al., "Present Status of the Use of Cytokines as Adjuvants with Vaccines to Protect Against infectious Diseases", Clin. Infect. Dis., vol. 21, No. 6, 1995, pp. 1439-1449.

Y. Tanio, Partial Englis Translation of Japanese Journal of Cancer and Chemotherapy, vol. 7, No. 9, pp. 1710-1718, 1980.

T. Azuma, et al., "Indentification of a Novel WT1-Derived Peptide Which Induces Human Leucocyte Antigen-A24-Restricted Anti-Leukaemia Cytotoxic T Lymphocytes", British Journal of Haematology, 2002, 116, pp. 601-603.

The 31st Annual Meeting of the Japanese Society for Immunology, pp. 160, 2-C-W11-8-P Abstract enclosed, 2001.

S. Rosenberg, et al., "A New Era for Cancer Immunotherapy Based on the Genes that Encode Cancer Antigens", Immunity, vol. 10, pp. 281-287, Mar. 1999.

A. Bakker, et al., Melanocyte Lineage-Specific Antigen gp 100 is Recognized by Melanoma-Derived Tumor-Infiltrating Lymphocytes, The Journal of Experimental Medicine, vol. 179, Mar. 1994, pp. 1005-1009.

Y. Kawakami, et al., "Cloning of the Gene Coding for a Shared Human Melanoma Antigen Recognized by Autologous T Cells Infiltrating into Tumor", Proc. Natil. Acad. Sci., USA, vol. 91, pp. 3515-3519, Apr. 1994.

V. Brichard, et al., "The Tyrosinase Gene Codes for an Antigen Recognized by Autologous Cytolytic T Lymphocytes on HLA-A2 Melanomas", Journal of Experimental Medicine, vol. 178, Aug. 1993, pp. 489-495.

B. Fisk, et al., "Identification of an Immunodominate Peptide of HER-2/neu Protooncogene Recognized by Ovarian Tumor-specific Cytotoxic T Lymphocyte Lines", Journal of Experimental Medicine, vol. 181, Jun. 1995, pp. 2109-2117.

K. Tsang, et al., "Generation of Human Cytotoxic T Cells Specific for Human Carcinoembryonic Antigen Epitopes from Patients Immunized with Recombinant Vaccinia-CEA Vaccine", Journal of the National Cancer Institute, vol. 87, No. 13, Jul. 5, 1995, pp. 982-990.

P. Correale, et al., "In Vitro Generation of Human Cytotoxic T Lymphocytes Specific for Peptides Derived from Prostate-Specific Antigen", Journal of the National Cancer Institute, vol. 89, No. 4, Feb. 19, 1997.

K. Call, et al., "Isolation and Characterization of a Zinc Finger Polypeptide Gene at the Human Chromosome 11 Wilms' Tumor Locus", Cell, vol. 60, Feb. 9, 1990, pp. 509-520.

N. Nanda, et al., "Induction of Anti-Self-Immunity to Cure Cancer", Cell, vol. 82, Jul. 14, 1995, pp. 13-17.

* cited by examiner

Fig. 2
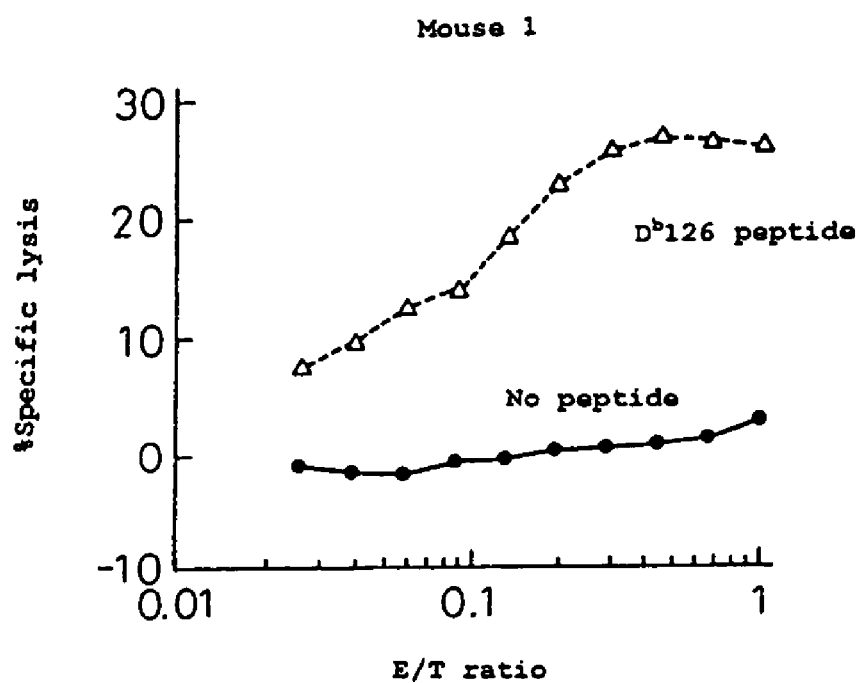
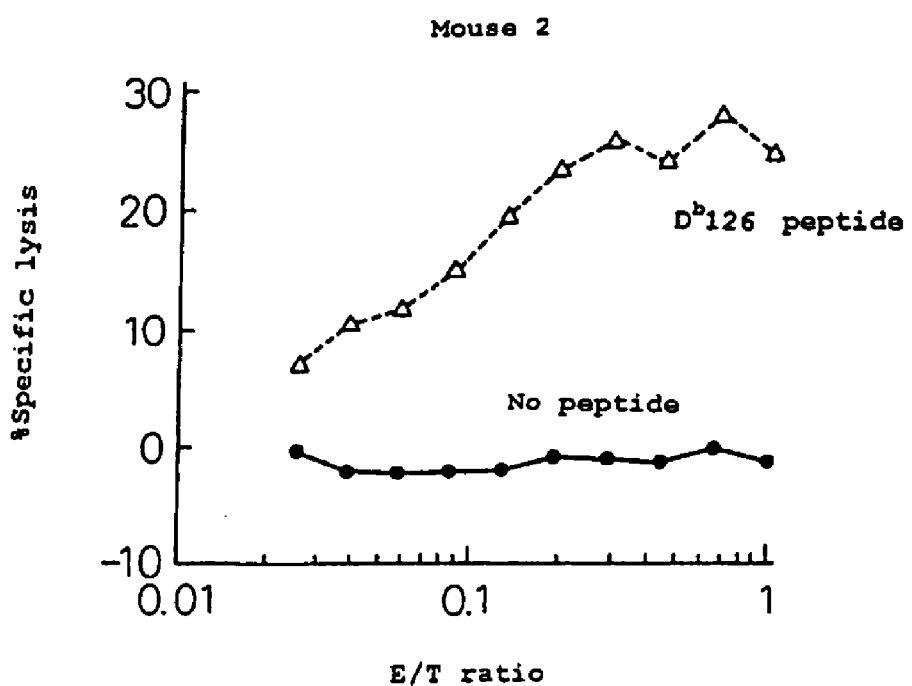

Fig.3
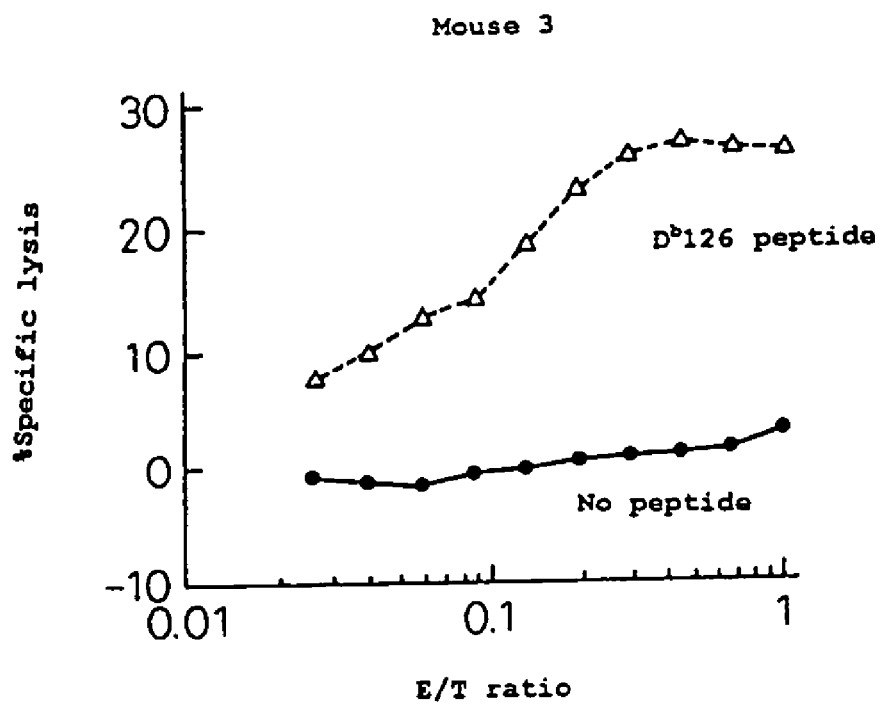
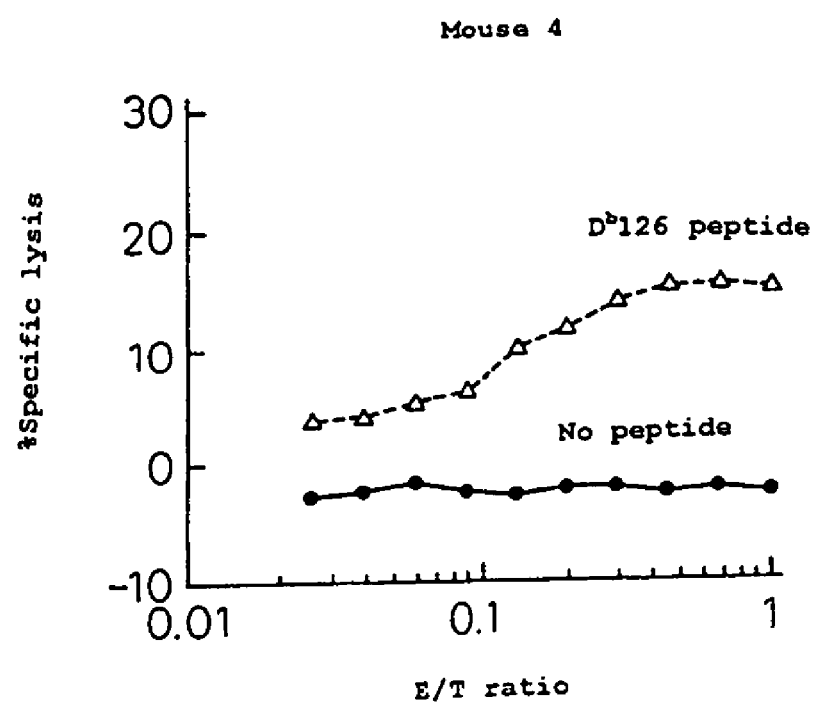

Fig. 5
CD19 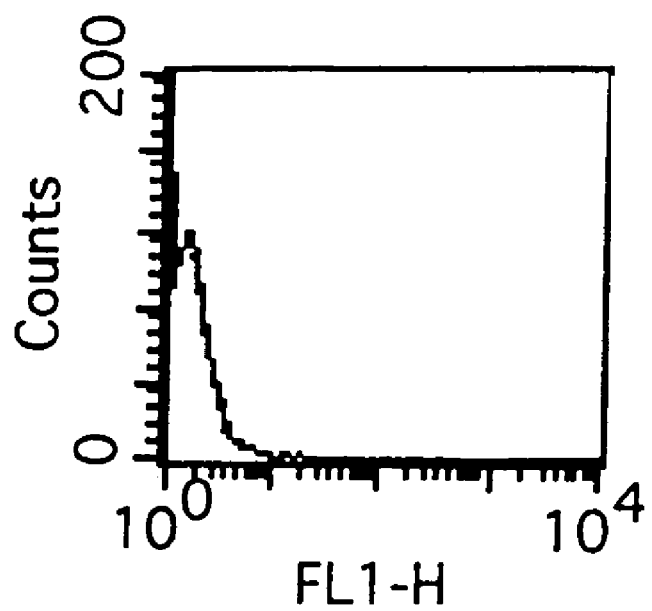
CD3 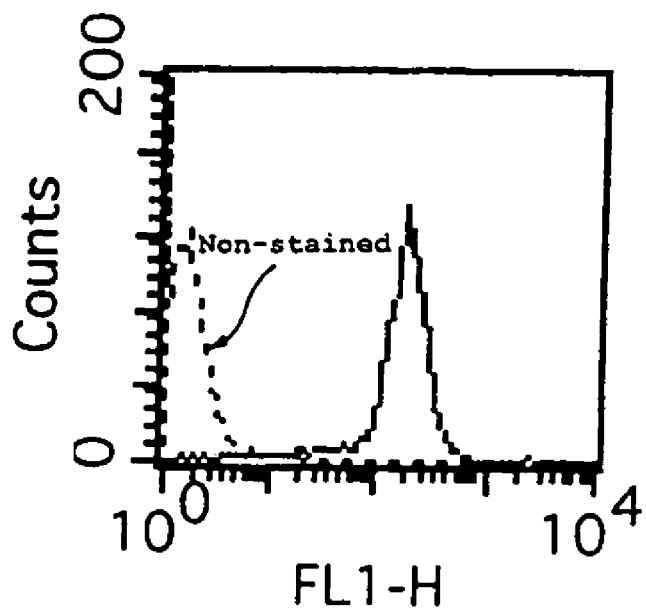

Fig. 6
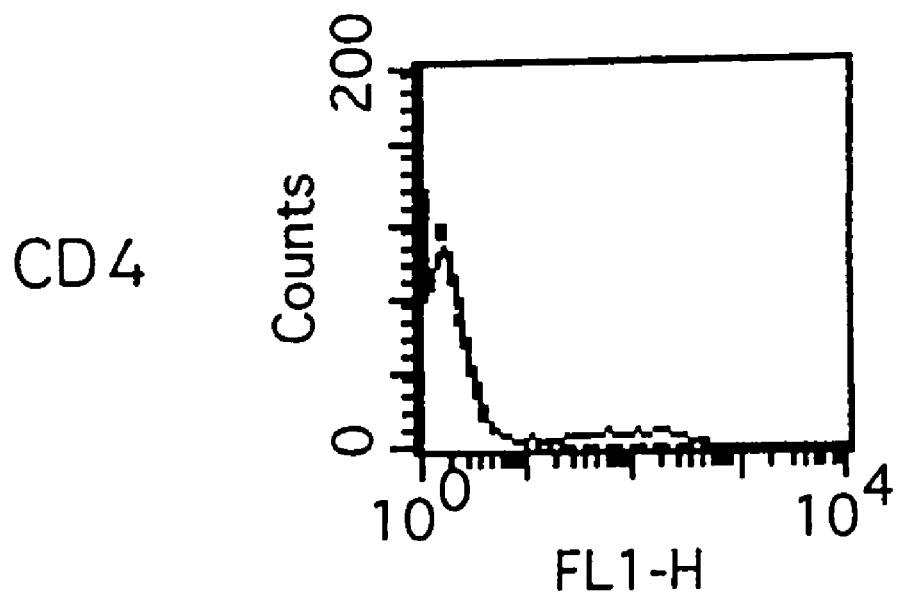
CD4
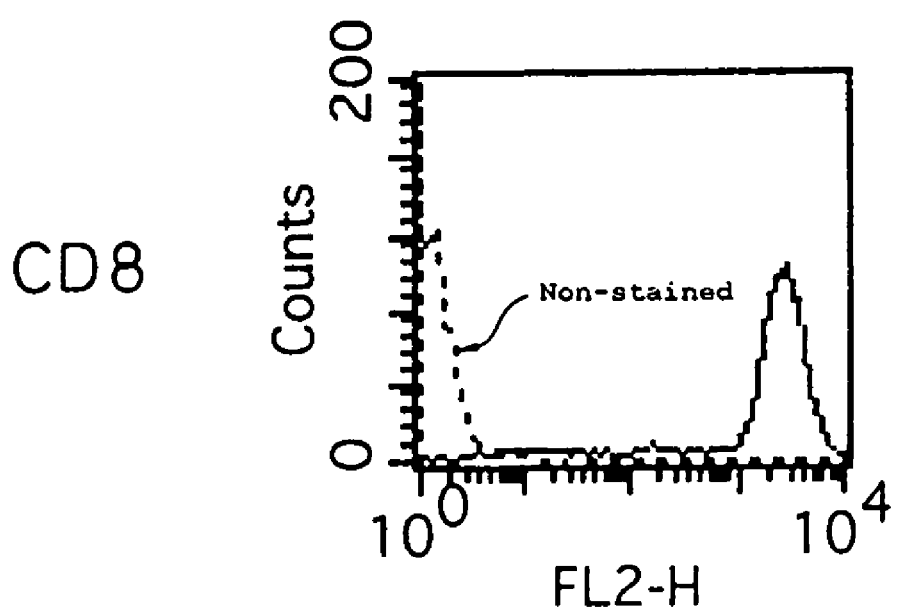
CD8

Fig. 8
CD19
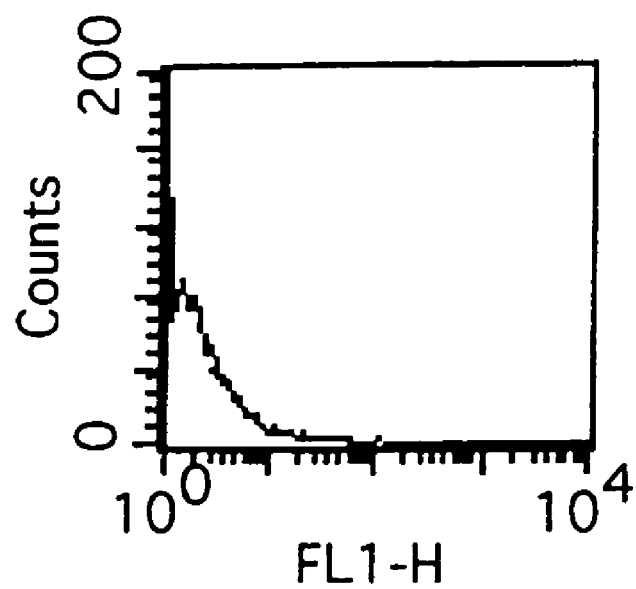
CD3
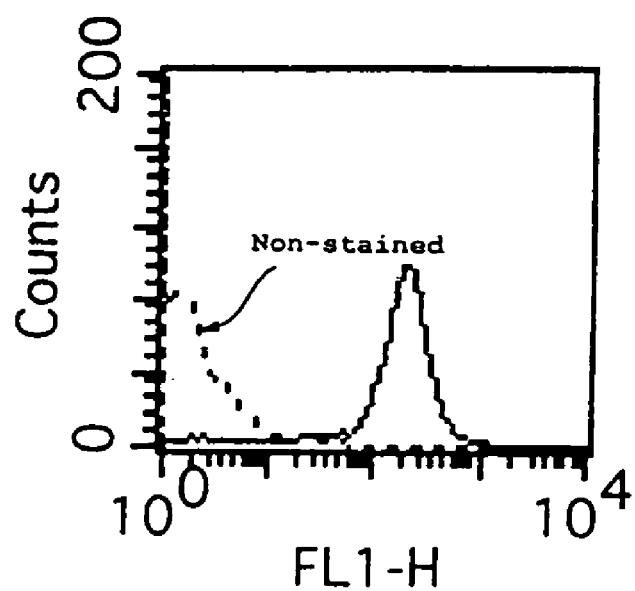

Fig. 9
CD4
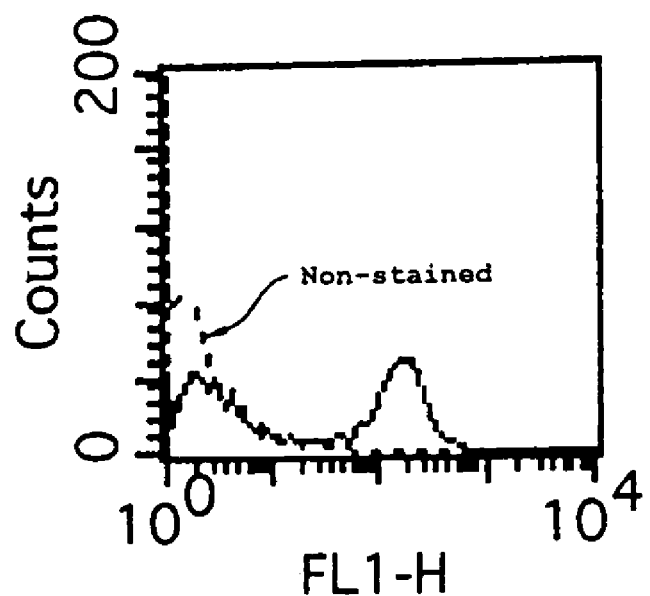
CD8
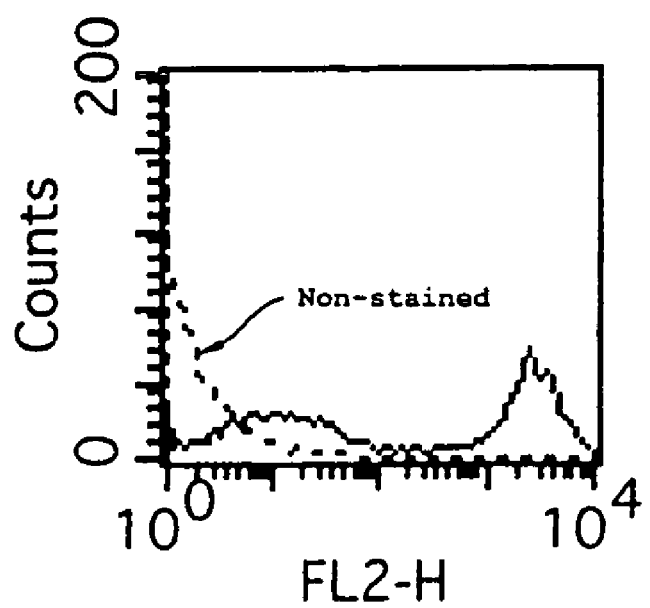

U.S. 7,517,950 B2

TUMOR ANTIGEN BASED ON PRODUCTS OF THE TUMOR SUPPRESSOR GENE WT1

CONTINUATION DATA

This application is a Continuation of prior U.S. application Ser. No. 09/744,815, filed Jan. 30, 2001, pending, which is the national stage of PCT/JP99/04130, filed Jul. 30, 1999.

TECHNICAL FIELD

The present invention relates to tumor antigens based on the products of WT1, the tumor suppressor gene of Wilms tumor. The tumor antigens are useful as anti-cancer vaccines against tumors of the blood such as leukemia, myelodysplastic syndromes, multiple myeloma, and malignant lymphoma, or solid tumors such as gastric cancer, colon cancer, lung cancer, breast cancer, germ cell tumor, hepatic cancer, skin cancer, bladder cancer, prostate cancer, uterine cancer, cervical cancer, and ovarian cancer, as well as all cancers that express WT1.

BACKGROUND ART

The immunological mechanisms to reject foreign material are generally comprised of: the humoral immunity which involves macrophages that recognize antigens and function as antigen presenting cells, helper T cells that activate other T cells etc. by recognizing antigen presented by said macrophages and then producing various cytokines, B cells that differentiates into antibody-producing cells by the action of said lymphokines etc., as well as the cellular immunity in which killer T cells that undergo differentiation in response to antigen presentation, and attack and destroy the target cells.

At present, cancer immunity is mainly considered to be derived from cellular immunity in which killer T cells participate. In the killer T cell-involved cancer immunity, precursor T cells that recognized tumor antigen presented in the form of a complex between the major histocompatibility complex (MHC) class I and the tumor antigen differentiate and propagate to produce killer T cells, which attack and destroy tumor cells. At this time, tumor cells present, on the surface thereof, the complex of the MHC class I antigen and the tumor antigen, which is targeted by the killer T cells (Cur. Opin. Immunol., 5: 709, 1993; Cur. Opin, Immunol, 5: 719, 1993; Cell, 82: 13, 1995; Immunol. Rev., 146: 167, 1995).

The above tumor antigen presented by the MHC class I antigen on the surface of the target tumor cells is considered to be a peptide composed of about 8 to 12 amino acids produced after the antigen protein synthesized in the tumor cells underwent processing by intracellular proteases (Cur. Opin. Immunol., 5: 709, 1993; Cur. Opin, Immunol, 5: 719, 1993; Cell, 82: 13, 1995; Immunol. Rev., 146: 167, 1995).

Currently, antigen proteins are being searched for various cancers, but few have been demonstrated as cancer specific antigens.

WT1, a Wilms tumor suppressor gene (WT1 gene) was isolated from chromosome 11p13 as one of the causative genes of Wilms tumor based on the analysis of the WAGR syndrome that was complicated by Wilms tumor, aniridia, urogenital anomaly, mental retardation, etc. (Gessler, M. et al., Nature, 343: 774-778 (1990)), and the genomic DNA is about 50 Kb and is composed of ten exons, of which cDNA is about 3 kb. The amino acid sequence deduced from the cDNA is as set forth in SEQ ID NO: 1 (Mol. Cell. Biol., 11: 1707, 1991).

From the facts that the WT1 gene is highly expressed in human leukemia and that the treatment of leukemia cells with WT1 antisense oligomers results in suppression of cellular growth (Japanese Unexamined Patent Publication (Kokai) No. 9-104627), the WT1 gene has been suggested to promote the growth of leukemia cells. Furthermore, WT1 was found to be highly expressed in solid tumors such as gastric cancer, colon cancer, lung cancer, breast cancer, lung cell cancer, hepatic cancer, skin cancer, bladder cancer, prostate cancer, uterine cancer, cervical cancer, and ovarian cancer (Japanese Patent Application (Tokugan) 9-191635), and the WT1 gene was demonstrated to be a new tumor marker in leukemia and solid tumors. However, it has not been confirmed that the expression products of the WT1 gene are tumor-specific antigens useful as a cancer vaccine.

DISCLOSURE OF THE INVENTION

Thus, the present invention intends to confirm the possibility that the expression product of the WT1 gene is a tumor antigen and to provide a new tumor antigen.

After intensive research to resolve the above problems, the inventors of the present invention have synthesized polypeptides having 7 to 30 contiguous amino acids containing at least one amino acid that is expected to function as an anchor amino acid in the binding with mouse and human MHC class I and MHC class II in the amino acid sequence of the expression product of the WT1 gene, confirmed that these peptides bind to MHC proteins and, when bound to the MHC class I antigen, induce killer T cells and exert cytocidal effects on the target cell, and thereby have completed the present invention.

Thus, the present invention provides a tumor antigen comprising an expression product of mouse WT1 or a portion thereof. According to a preferred embodiment, the present invention provides a tumor antigen that comprises, as an active ingredient, a peptide having 6 to 30 amino acids containing an anchor amino acid required for binding to the MHC molecules in the amino acid sequence as set forth in SEQ ID NO: 1 that corresponds to the cDNA of WT1.

Furthermore, the present invention provides a tumor antigen that comprises, as an active ingredient, a peptide having 7 to 30 amino acids containing an anchor amino acid for binding to the MHC molecules in the amino acid sequence as set forth in SEQ ID NO: 2 that corresponds to the cDNA of human WT1.

The present invention also provides a cancer vaccine comprising the above tumor antigen.

BRIEF DESCRIPTION OF DRAWINGS

FIG. 2 is a graph that compares the cytocidal effect of the cells immunized with the $D^b$ 126 peptide on the target cells pulsed with $D^b$ 126 peptide and the non-pulsed target cells in Example 2.

FIG. 3 is a graph having the same meaning as in FIG. 2.

FIG. 5 is a chart showing the result of FACS analysis on the surface markers of CTL induced by the $D^b$ 126 peptide (CD19 cells and CD3 cells).

FIG. 6 is a similar chart to FIG. 5 with respect to the CD4 cells and the CD8 cells.

FIG. 8 is a chart showing the result of FACS analysis on the surface markers of CTL induced by the WH 187 peptide (CD19 cells and CD3 cells).

FIG. 9 is a chart similar to FIG. 8 with respect to the CD4 cells and the CD8 cells.

BEST MODE FOR CARRYING OUT THE INVENTION

Figure 1:
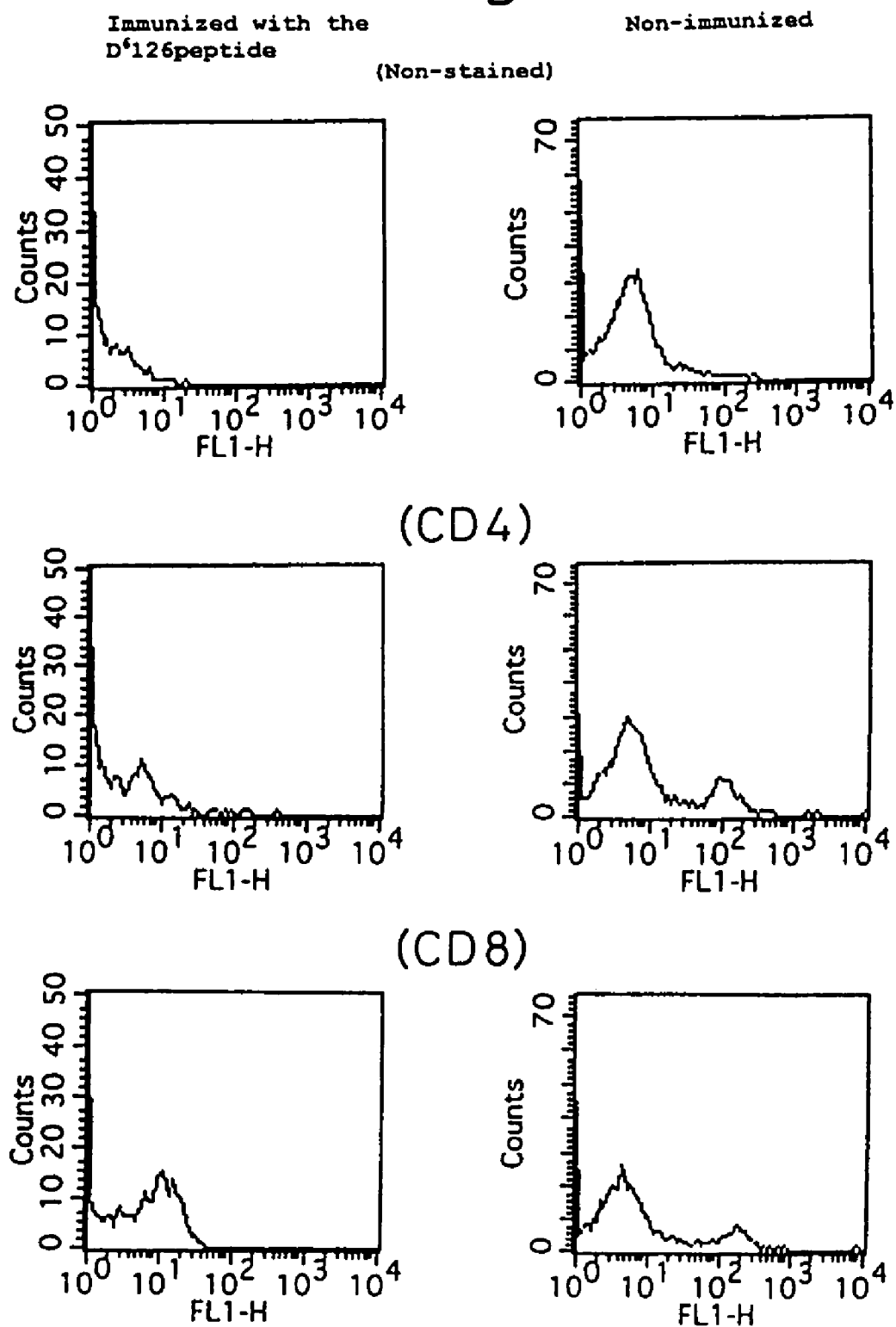
FIG. 1 is a graph showing a ratio of $CD4^+$ and $CD8^+$ cells in flow cytometry on the cells immunized with the $D^b$ 126 peptide and non-immunized cells in Example 1.

In accordance with the present invention, $K^b$ and $D^b$ of mouse MHC class I and A* 0201 of human HLA were selected as a basis for designing tumor antigen peptides, and peptides expected to have a high affinity with them were selected.

Based on the description in Immunogenetics 41: 178-228 (1995), Phe and Tyr at position 5 and Leu and Met at position 8 etc. are expected to be anchor amino acids for binding to $K^b$, and Asn at position 5 and Met and Ile at position 9 etc. are expected to be anchor amino acids for binding to $D^b$.

It is also known that the size of the tumor antigen peptide presented by MHC class I on the surface of tumor cells is about 8 to 12. Therefore, the tumor antigen peptide of the present invention is a peptide having 7 to 30 contiguous amino acids containing an anchor amino acid in the amino acid sequence of the WT1 gene expression product as set forth in SEQ ID NO: 1. The number of amino acids is preferably 8 to 12, for example 8 or 9.

As a specific embodiment in the present invention, the following peptides comprising 8 amino acids:

$K^b$ 45 Gly Ala Ser Ala Tyr Gly Ser Leu (SEQ ID NO: 3), and $K^b$ 330 Cys Asn Lys Arg Tyr Phe Lys Leu (SEQ ID NO: 4)

were used as peptides binding to $K^b$ of MHC class I, and the following peptides comprising 9 amino acids:

$D^b$ 126 Arg Met Phe Pro Asn Ala Pro Tyr Leu (SEQ ID NO: 5), $D^b$ 221 Tyr Ser Ser Asp Asn Leu Tyr Gln Met (SEQ ID NO: 6), and $D^b$ 235 Cys Met Thr Trp Asn Gln Met Asn Leu (SEQ ID NO: 7)

were used as peptides binding to $D^b$ of MHC class I. The underlined amino acids in the above sequences are those amino acids that are expected to function as anchors.

Then, among these peptides, for $K^b$ 45 and $K^b$ 330 the binding activity with $K^b$ of MHC class I was measured, and for $D^b$ 126, $D^b$ 221 and $D^b$ 235 the binding activity with $D^b$ of MHC class I was measured using the cell line (RMA-S) that does not express the endogenous antigen peptide (empty) and the cell line (RMA-S) that expresses $K^b$ and $D^b$ molecules.

Thus, RMA-S was cultured at 26° C. to effect high expression of MHC class I, and the cultured cells were incubated with the solutions of the test peptides at 37° C. for 1 hour. This makes unstable the MHC molecule that does not bind to the peptide leading to their disappearance from the cell surface and leaving MHC class I molecules alone that bound to the peptide. Then using fluorescently labeled monoclonal antibody that recognizes MHC class I ($K^b$, $D^b$), RMA-S cells were stained. Finally, the binding dissociation constant was calculated from the average amount of fluorescence per cell (Immunol. Lett., 47: 1, 1995).

As a result, the following result was obtained:

$K^b$ 45-4.5784838 (log)

$K^b$ 330-5.7617732

$D^b$ 126-6.2834968

$D^b$ 221-5.7545398

$D^b$ 235-6.1457624

As hereinabove stated, both have a strong to moderate binding affinity (Kd value) with $K^b$ or $D^b$, and the $D^b$ 126 peptide having the highest binding affinity was used in the following experiment.

For humans also, based on the description in Immunogenetics 41: 178-228 (1995), Leu and Met at position 2 from the N-terminal and Val and Leu at position 9 from he N-terminal are expected to be anchor amino acids for binding to HLA-A* 0201. Thus, the following two peptides having 9 amino acids that meet the above requirement were synthesized in the amino acid sequence of human WT1 protein (Mol. Coll. Biol., 11: 1707-1712, 1991) (SEQ ID NO: 2):

$D^b$ 126; Arg Met Phe Pro Asn Ala Pro Tyr Leu (SEQ ID NO: 5)

(the same as the sequence. Of $D^b$ 126 in mouse)

WH 187; Ser Leu Gly Glu Gln Gln Tyr Ser Val (SEQ ID NO: 8)

(anchor amino acids are underlined).

The binding activity of the above peptides with HLA-A* 0201 was measured as follows:

The above peptides and T2 cells having the empty HLA-A* 0201 molecules (J. Immunol., 150: 1763, 1993; Blood, 88: 2450, 1996) were incubated at 37° C. for 1 hour, and then the T2 cells were stained with fluorescently labeled monoclonal antibody that recognizes HLA-A2.1 to calculate the binding dissociation constant based on the average amount of fluorescence per cell in the FACS analysis.

| Binding activity | |
| --- | --- |
| Peptide | Kd (M) |
| $D^b$ 126 | $1.89 \times 10^{-6}$ |
| WH 187 | $7.61 \times 10^{-6}$ |

The two peptides have a binding affinity of moderate degree or higher.

Using the above $D^b$ 126 and WH 187 as a peptide that can combine with human MHC Class I molecules, the experiment described hereinafter was performed.

The present invention also relates to a cancer vaccine comprising the above antigen as an active ingredient. This vaccine can be used for prophylaxis or treatment of tumors of the blood such as leukemia, myelodysplastic syndromes, multiple myeloma, and malignant lymphoma, or solid tumors such as gastric cancer, colon cancer, lung cancer, breast cancer, germ cell tumor, hepatic cancer, skin cancer, bladder cancer, prostate cancer, uterine cancer, cervical cancer, and ovarian cancer. The vaccine can be given via oral or parenteral administration such as intraperitoneal, subcutaneous, intradermal, intramuscular, intravenous, and nasal administration.

As a method of administering the vaccine of the present invention, there can be used a method, in which mononuclear cells are collected from the patient's peripheral blood, from which dendritic cells are removed, and the peptide of the present invention is pulsed thereto, which is then returned to the patient via subcutaneous administration etc.

Vaccines can contain, in addition to the peptide given as the above active ingredient, pharmaceutically acceptable carriers for example suitable adjuvants such as a mineral gel like aluminum hydroxide; a surfactant such as lysolecithin, pluronic polyol; a polyanions; a peptide; or an oil emulsion. Alternatively, other aggregates that can be mixed into liposomes or blended into polysaccharides and/or vaccines can be used. The dosage is generally 0.1 µg to 1 mg/kg per day.

In the present invention, DNA encoding the above polypeptide vaccine can also be used as a vaccine (DNA vaccine). Thus, after a nucleic acid encoding WT1 or a portion thereof, preferably DNA, is inserted to a suitable vector, preferably an expression vector, it is administered to an animal to produce cancer immunity. A specific example is shown in Example 9.

EXAMPLES

Then, the following examples will demonstrate that the peptide of the present invention is useful as a tumor antigen or a cancer vaccine.

Example 1

One hundred µg of the $D^b$ 126 peptide, 200 µg of porcine lactate dehydrogenase and 0.5 ml of Freund's incomplete adjuvant were intraperitoneally injected to C57BL/6 mice twice every week for immunization treatment. One week after the immunization treatment, the mouse spleen was extracted, from which suspensions of spleen cells were prepared. On the other hand, the irradiated spleen cells of the syngeneic mice pulsed with the $D^b$ 126 peptide were incubated with a solution containing 50 µg/ml peptide at 37° C. for 30 minutes, which was used as the antigen presenting cell.

The above immunized spleen cells and the irradiated spleen cells were co-cultured for 5 days to induce or prepare killer T cells. On the other hand, using the Europium labeled EL-4 cells (expressing $K^b$ and $D^b$) pulsed with the $D^b$ 126 peptide (incubated at 37° C. for 30 minutes with a 100 µg/ml peptide solution) as the target cell in a standard method, a killing assay was performed in the following procedure (Table 1).

As a result, when the EL-4 cells pulsed with $D^b$ 126 were used as the target, cytocidal effects were observed, but when the EL-4 cells not pulsed with $D^b$ 126 were used as the target, few cytocidal effects were observed.

TABLE 1

| | Mouse A | Mouse B |
| --- | --- | --- |
| Peptide+ | 76.6% | 37.2% |
| Peptide− | 4.9% | 0.9% |

E/T ratio 40:1

Then, the spleen samples that exhibited significant cytocidal effects in the killing assay were stained with the fluorescently labeled anti-CD4 antibody or anti-CD8 antibody, which were then subjected to flow cytometry to analyze the expression of CD4 and CD8.

As a result, as shown in FIG. 1, in the spleen cells immunized with the $D^b$ 126 peptide, there was an increase in the CD8$^+$ cells represented by the killer T cells and the ratio of the CD8$^+$ cells to the CD4$^+$ cells represented by the helper T cells etc. was inversely increased compared to the non-immunized control spleen cells.

Example 2

Dendritic cells (DC) derived from the bone marrow of the C57BL/6 mice were prepared in the following manner. According to the standard method, the bone marrow cells were cultured in the presence of GM-CSF to prepare bone marrow-derived dendritic cells (J. Exp. Med. 182: 255, 1995).

The dendritic cells cultured for 7 days, 10 µM OVAII (Ovalbumin II) and 1 µM $D^b$ 126 peptide were incubated for 3 hours and then washed.

Then, the above DC cells were intradermally injected to the foot pads and hands of C57BL/6 mice, and on day 5 the lymph nodes were removed to prepare cell suspensions. On the other hand, the B7.1-RMA-S cells (RMA-S cells transfected with a gene encoding B7.1 which is a co-stimulatory molecule) pulsed with $D^b$ 126 and irradiated were prepared.

Then the above cell suspension derived from the relevant lymph node and the B7.1-RMA-S cells were mixed and cultured for in vitro restimulation.

Then, on day 5 after the in vitro restimulation, a killing assay was performed using the $^{51}$Cr-labeled RMA-S cells as the target. When ⅛ of the total lymphocytes recovered on day 5 after restimulation was used as the effector cell, the E/T ratio was set as the highest one (1.0).

As shown in FIGS. 2 and 3, the effector cells derived from the lymph nodes of the mice immunized with the $D^b$ 126 peptide killed the target cells pulsed with said peptide but did not kill the target cells that were not pulsed with said peptide.

Analysis of the ratio of the CD4$^+$ cells and the CD8$^+$ cells by flow cytometry performed as in Example 1 shows that CD4:CD8=1:1.4 to 1.7 and that in the mouse cells immunized with the $D^b$ 126 peptide the CD8$^+$ cells were increased and the ratio of the CD4$^+$ cells:the CD8$^+$ cells (about 2:1 in the control cells) was reversed in the cells immunized with the $D^b$ 126 peptide as compared to the non-immunized mouse (control) cells.

Example 3

T2 cells (5×10$^4$) that were irradiated after incubating for 1 hour with the peptide D$^b$ 126 or WH 187 (40 μg/ml) and the peripheral blood mononuclear cells (1×10$^6$) from a healthy human having HLA-A* 0201 were co-cultured. One week later, T2 cells that were irradiated after incubating for 1 hour with the peptide (20 μg/ml) were added to the above culture system for restimulation. From the following day, human IL-2 (final concentration 100 JRU/ml) was added to the culture.

Subsequently, after repeating, for five times, stimulation with the T2 cells that were irradiated after being pulsed with the peptide, a killing assay was performed using, as the target, the T2 cells pulsed with the peptide or the T2 cells not pulsed with the peptide. The surface markers of the induced CTL were subjected to FACS analysis.

The killing assay was performed according to the standard method using, as the target, the Europium-labeled T2 cells pulsed with the peptide.

Figure 4:
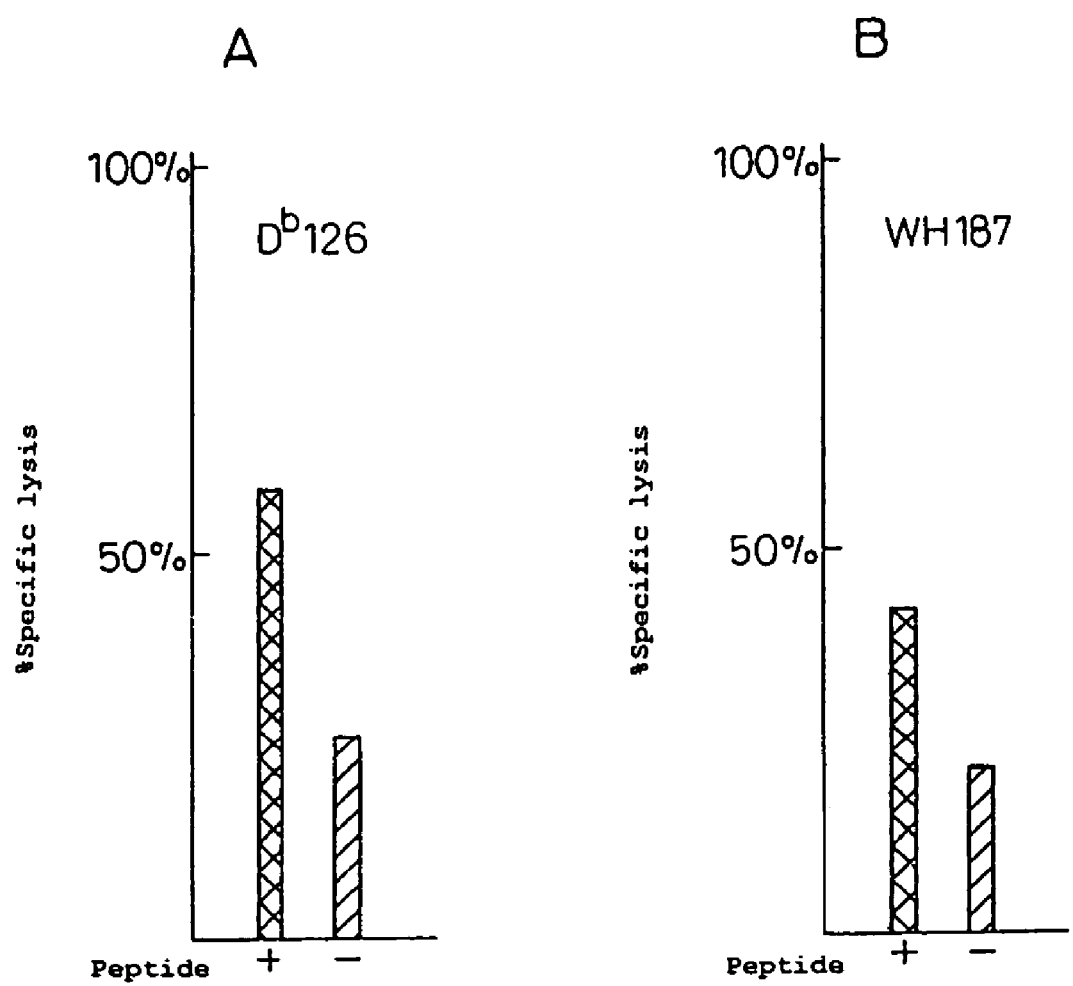
FIG. 4 is a graph in which A represents the cytocidal effect of CTL induced by the $D^b$ 126 peptide on the T2 cells pulsed with the $D^b$ 126 peptide in Example 3, and B represents the cytocidal effect of CTL induced by the WH 187 peptide on the T2 cells pulsed with the WH 187 peptide in Example 3.

Effector:Target ratio (E/T ratio) is 10:1
Co-cultivation time: 3 hours
The concentration of the peptide in the culture: 5 μg/ml The result is shown in FIG. 4. A in FIG. 4 shows the cytocidal effect of CTL induced using D$^b$ 126 peptide on the T2 cells pulsed with the D$^b$ 126 peptide, and B in FIG. 4 shows the cytocidal effect of CTL induced using the WH 187 peptide on the T2 cells pulsed with the WH 187 peptide.

In either case, more potent cytocidal effects were observed in the T2 cells pulsed with the peptide.

Figure 7:
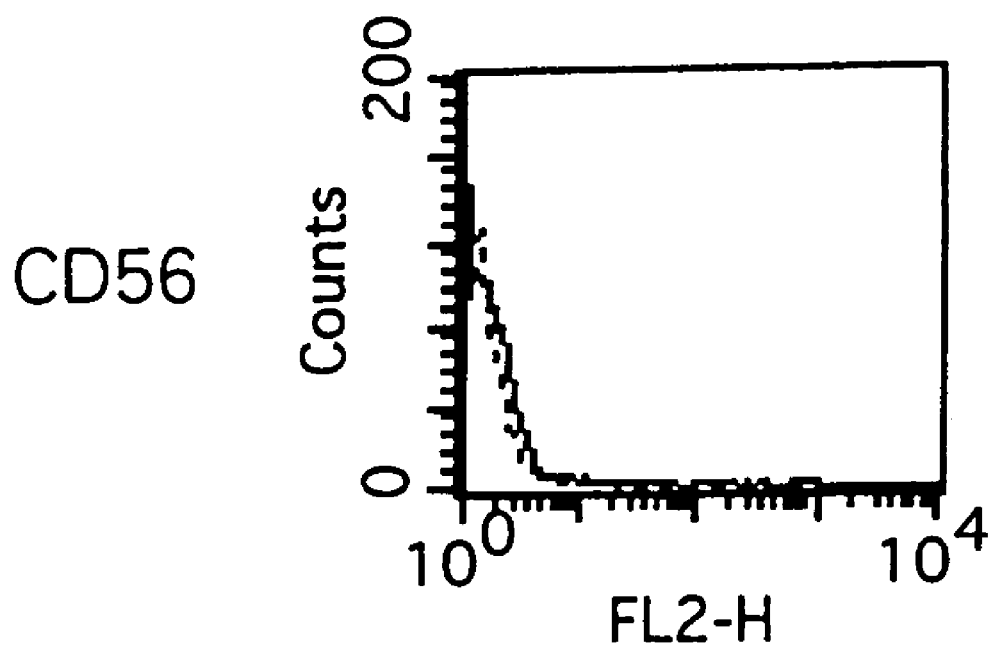
FIG. 7 is a similar chart to FIG. 5 with respect to the CD56 cells.
Figure 10:
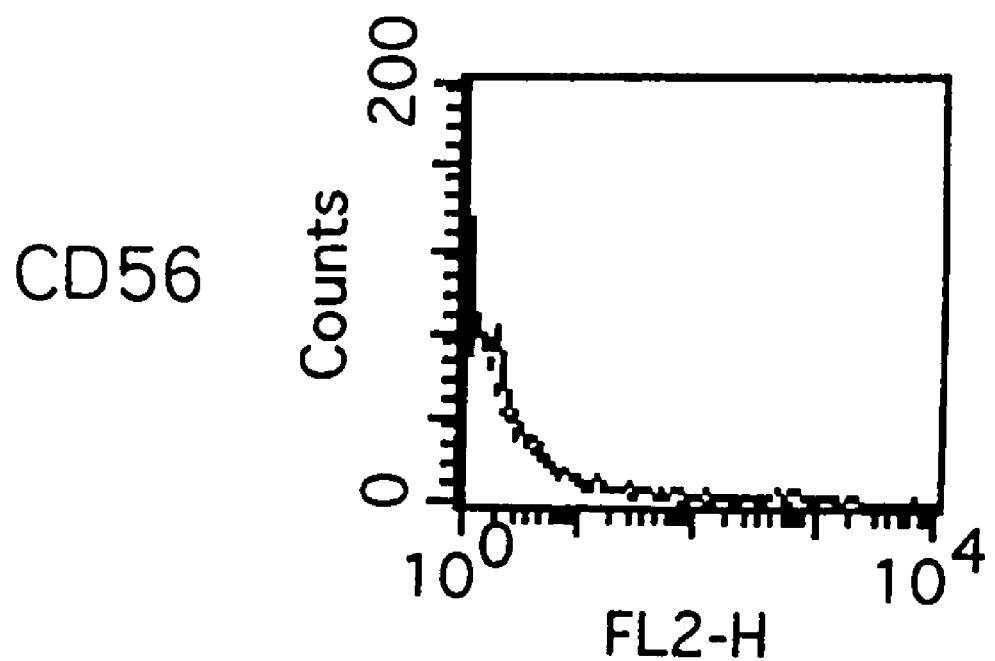
FIG. 10 is a chart similar to FIG. 8 with respect to the CD56 cells.

The results of FACS analysis are shown in FIGS. 5 to 10. FIGS. 5 to 7 show the results of human CTL induced with the D$^b$ 126 peptide, indicating that most of the cells were CD8-positive. FIGS. 8 to 10 show the results of human CTL induced with the WH 187 peptide. The CD4-positive cells and the CD8-positive cells were almost equal in the number.

Example 4

In order to test the MHC dependency of the cytolytic activity of the D$^b$ 126 peptide-specific CTL, anti-HLA-A2.1 monoclonal antibody was used to block the cytolytic activity of CTL on the T2 cells pulsed with the peptide. The specific cytolysis of the T2 cells pulsed with the D$^b$ 126 peptide was measured in the presence or absence of monoclonal antibody (BB7.2) that blocks HLA-A2.1 molecule at a E/T ratio of 5:1.

Figure 11:
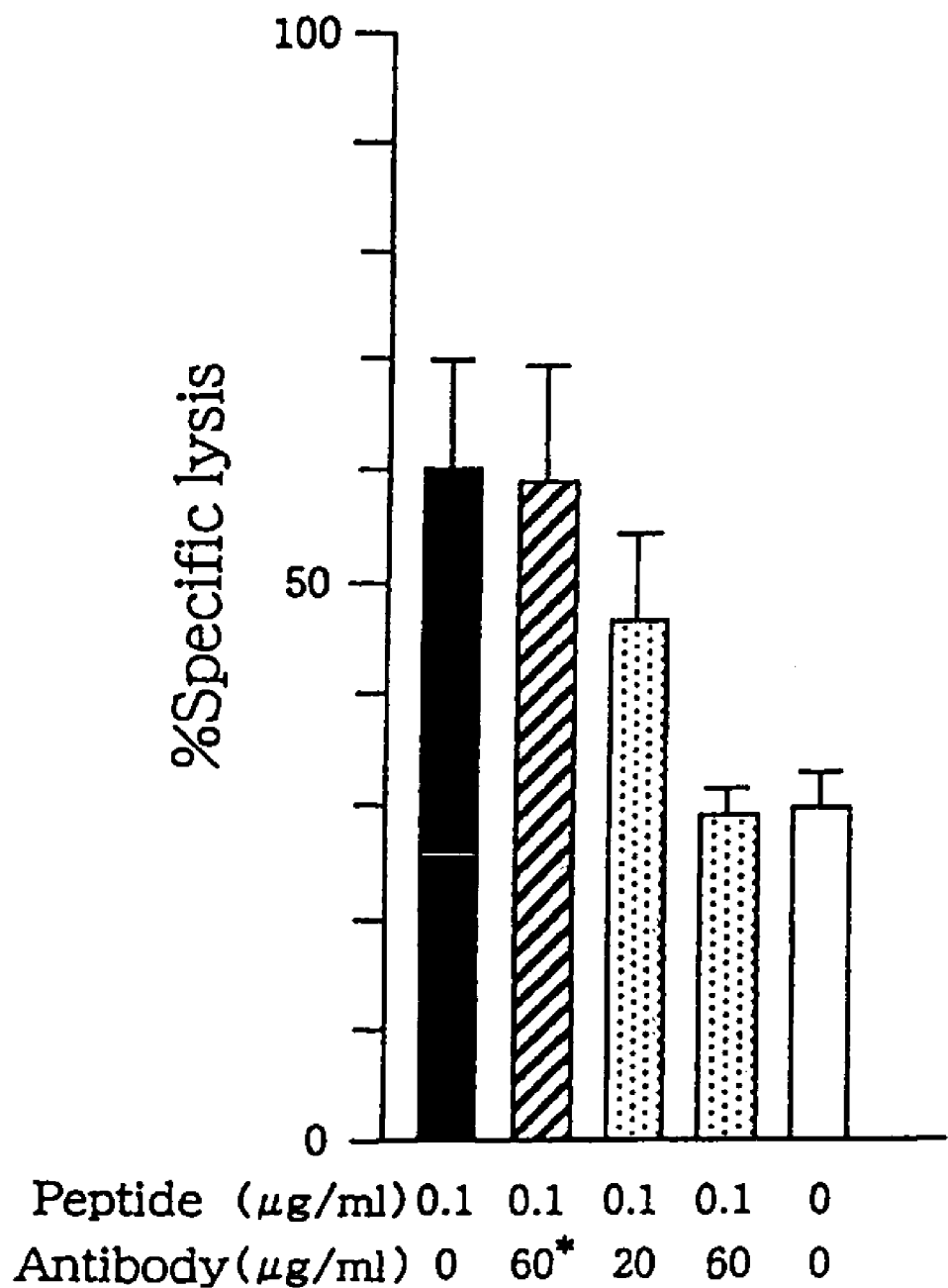
FIG. 11 is a graph showing the effect of anti-HLA-A2.1 antibody on the specific lysis of T2 cells pulsed with the $D^b$ 126 peptide by the $D^b$ 126 peptide-specific CTL.

The result is shown in FIG. 11. In the figure, the * symbol represents the result obtained using anti-H-2K$^b$ monoclonal antibody in stead of anti-HLA-A2.1 monoclonal antibody. As can be seen from the figure, the addition of 60 μg/ml of anti-HLA-A2.1 monoclonal antibody resulted in the reduction of the cytotoxicity to background of the cytolysis of the T2 cells. Unrelated monoclonal antibody (anti-H-2K$^b$ monoclonal antibody Y3) with the same isotype had no effects on the lysis of the T2 cells.

Example 5

It was tested whether the D$^b$ 126 peptide-specific CTL can kill the HLA-A2.1-positive leukemia cells that inherently express WT1. As the target cell, the TF1 cells (express WT-1, HLA-A2.1-positive), the JY cells (do not express WT-1, HLA-A2.1-positive), and the Molt-4 cells (express WT1, HLA-A2.1-negative) were used and cytotoxicity was measured at a E:T ratio of 7.5:1 (a) or 15:1 (b).

Figure 12:
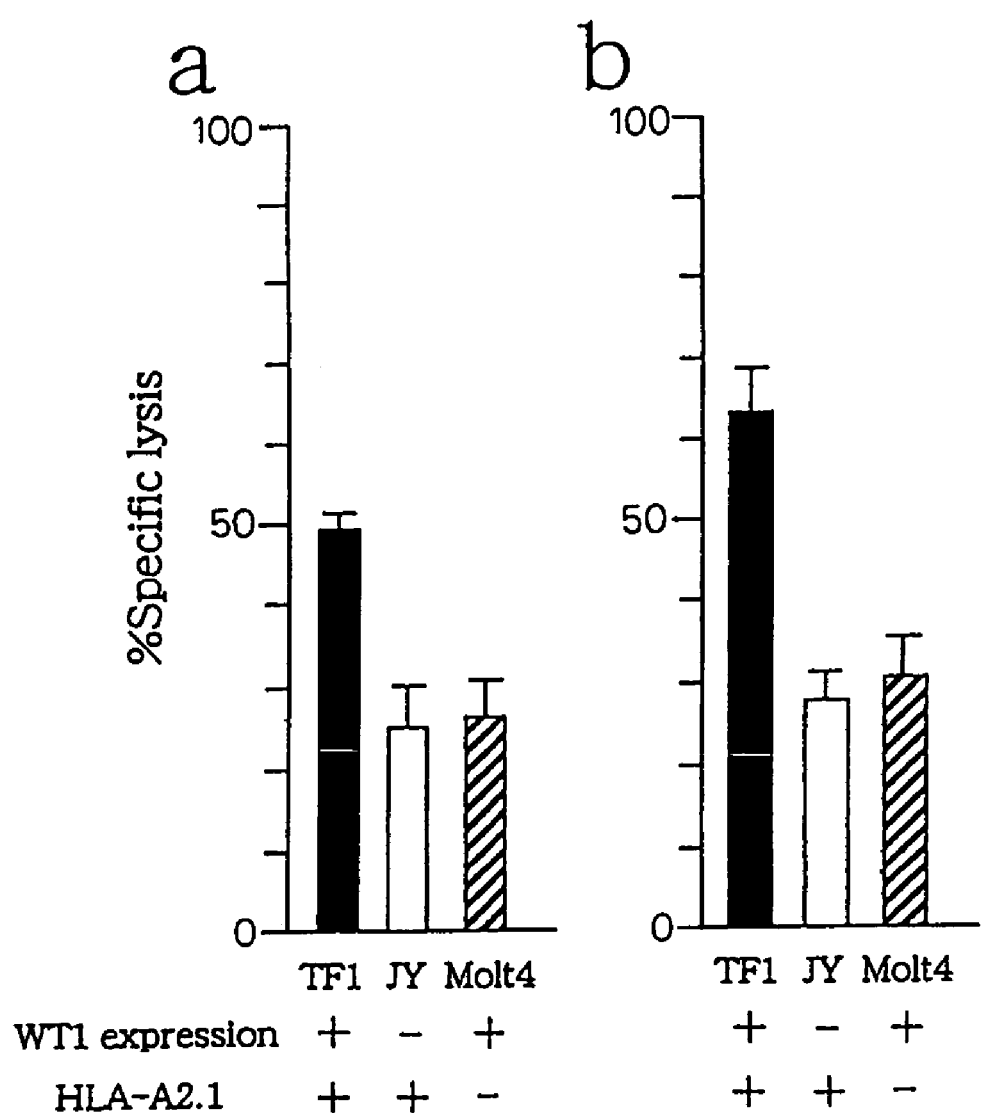
FIG. 12 is a graph comparing the lytic activity of the $D^b$ 126 peptide-specific CTL on the target cells expressing or not expressing WT1. In the figure, a shows the result obtained when the E:T ratio is 7.5:1 and b shows the result obtained when the E:T ratio is 15:1.

The result is shown in FIG. 12. The D$^b$ 126 peptide-specific CTL exhibited a significant cytotoxicity to the HLA-A2.1-positive leukemia cell TF1 that inherently expresses WT1, but exhibited a cytolysis of a background level to the Molt-4 (which expresses WT1, HLA-A2.1-negative) or the JY cells (which do not express WT1, HLA-A2.1-positive).

Example 6

It was tested whether the D$^b$ 126 peptide-specific CTL can recognize tumor cells that inherently express WT1 and can cause cytolysis thereof. Specific lysis was measured at the E/T ratio shown in FIGS. 13 and 14 for tumor cells (FLB3) that express WT1 and tumor cells (RMA) that do not express WT1 (FIG. 13) or for the C1498 cells transfected with the WT1 gene or the C1498 cells not transfected with the WT1 gene (FIG. 14).

Figure 13:
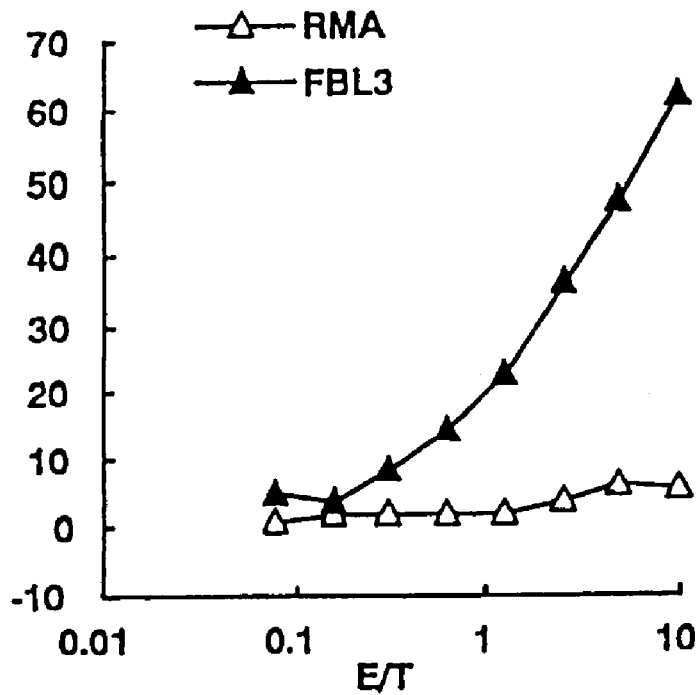
FIG. 13 is a graph that compares the lytic activity of the $D^b$ 126 peptide-specific CTL on the tumor cells (FBL3) that inherently express WT1 and the tumor cells (RMA) that do not express WT1.
Figure 14:
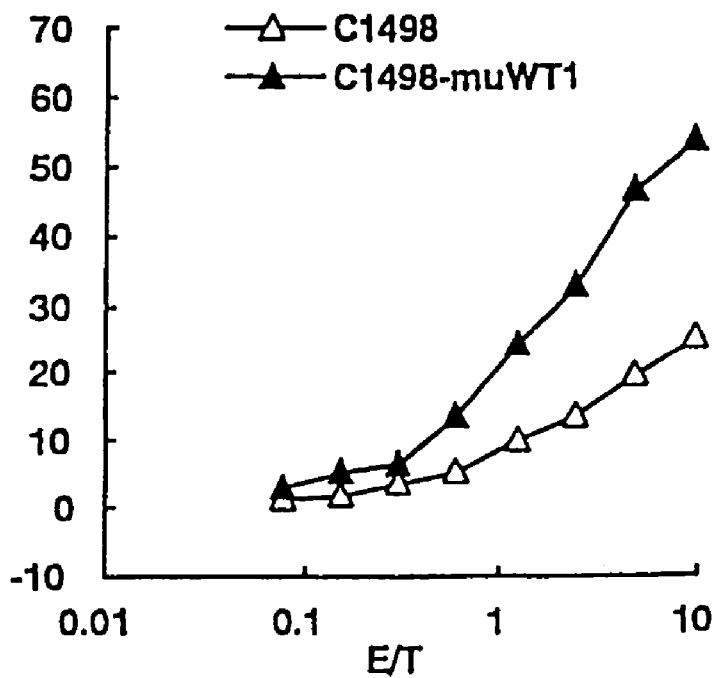
FIG. 14 is a graph that compares the lytic activity of the $D^b$ 126 peptide-specific CTL on the cells that were transformed with the WT1 gene and the same cells that were not transformed.

As shown in FIG. 13, the D$^b$ 126 peptide-specific CTL caused lysis of the FBL3 cells that inherently express WT1 but not the RMA cells that do not express WT1. As shown in FIG. 14, the D$^b$ 126 peptide-specific CTL further killed the C1498 cells transfected with the mouse WT1 gene as compared to the parent C1498 cells that do not express WT1. This confirmed that the molecule targeted for cell killing by CTL is indeed the WT1 peptide. These results suggest that the D$^b$ 126 peptide-specific CTL can recognize D$^b$ 126 peptide or the related peptides, which were naturally produced by the intracellular processing of the WT1 protein and presented on the H-2D$^b$ molecules of the WT1-expressing cells.

Example 7

In order to test whether the cytolytic activity of CTL is MHC dependent, measurement was performed in the presence of an antibody against the H-2 class I molecule. Thus, cytolytic activity of the D$^b$ 126 peptide-specific CTL against the RMA-S cells pulsed with the D$^b$ 126 peptide was measured in the presence of a titer-adjusted monoclonal antibody against H-2K$^b$ (28.13.3S), H-2D$^b$ (28.11.5S), or H-2L$^d$ (MA143). As the control monoclonal antibody, monoclonal antibody having the same isotype was used.

Figure 15:
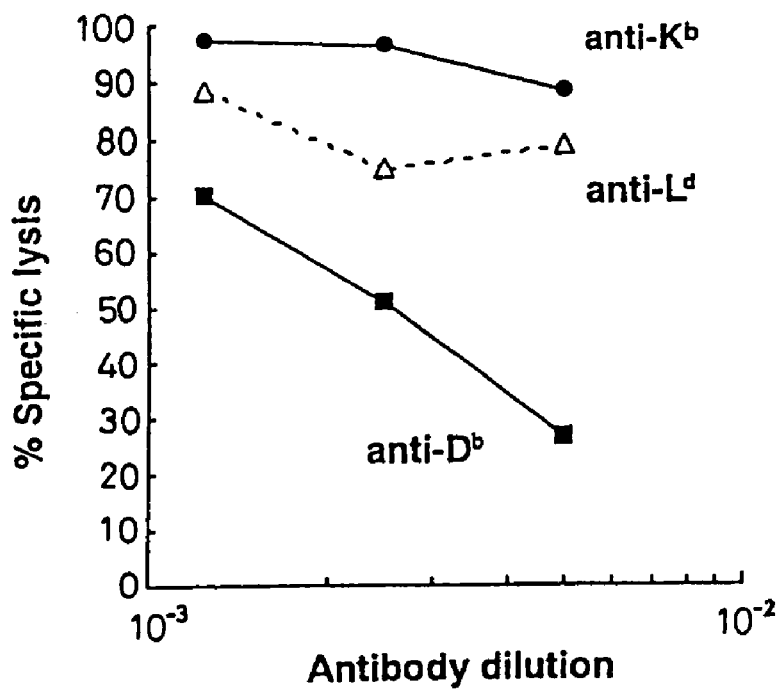
FIG. 15 is a graph showing the effect of anti-H-2$D^b$ antibody on the cytotoxicity of the $D^b$ 126 peptide-specific CTL.

The result is shown in FIG. 15. Depending on the increased concentrations of antibody against H-2D$^b$, the lytic activity of CTL against the RMA-S cells pulsed with the D$^b$ 126 peptide was suppressed, whereas antibodies against H-2K$^b$ or H-2L$^d$ did not suppress the lytic activity of CTL. These results indicate that CTL exhibits the cytolysis activity in a H-2D$^b$-dependent manner.

Example 8

It was tested whether in vivo tumor immunity can be elicited by the active immunization with the D$^b$ 126 peptide. Using the LPS-activated spleen cells (solid line in FIG. 16) pulsed with the D$^b$ 126 peptide, the LPS-activated spleen cells only (shaded line) or phosphate buffered saline (PBS) only (broken line), mice were immunized once every week. After immunization for 3 weeks, 3×10$^7$ FBL3 leukemia cells were intraperitoneally administered.

Figure 16:
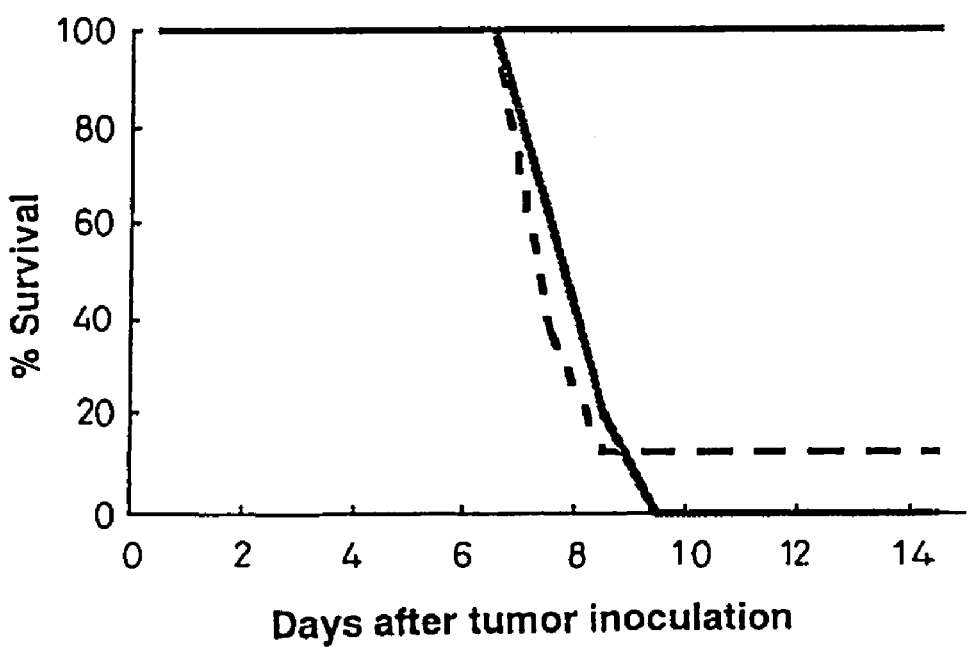
FIG. 16 is a graph showing the in vivo immunological effect when mice was immunized with the $D^b$ 126 peptide as a vaccine.

The result is shown in FIG. 16. The mice immunized with the D$^b$ 126 peptide overcame tumor challenge and survived, whereas the non-immunized mice and the mice immunized with the LPS-activated spleen cells could not reject tumor challenge and died. In both of the immunized and non-immunized mice, the presence of ascites was observed three days after the above intraperitoneal injection of tumor cells. Ascites continued to increase in the non-immunized mice, and the mice eventually died. In the immunized mice, on the other hand, ascites started to gradually decrease thereafter, and the mice completely rejected tumor challenge and survived. In the non-immunized mice, natural regression was occasionally observed. The regression is expected to be due to natural induction of CTL specific for Friend leukemia virus (FBL3 leukemia cells are transformed with this virus). Because such CTL induction has occasionally been observed in C57BL/6 mice.

Example 9

DNA Vaccine

One hundred μg of WT1-expressing plasmid DNA (plasmid that continuously expresses WT1 which was prepared by ligating the Sau 3AI fragment of mouse WT1 cDNA (Molecular and Cellular Biology, vol. 11, No. 3, p. 1707-1712 (1991), the left column on p. 1709) to the CMV-IE promoter) (Proc. Natl. Acad. Sci. USA., 92: 11105-11109 (1995)) was intramuscularly injected to 6 to 8 week old C57BL/6 mice every 10 days for a total of three times. Ten days after the last intramuscular injection, mouse spleens were removed to prepare spleen cells. After the spleen cells and mWT1C1498 cells (irradiated with 40 Gy radiation) expressing WT1 were co-cultured at 37° C. for 6 days, a killing assay (Europium-labeled) was performed using C1498 (PM5G-mWT1) that expressed WT1 and C1498 (PM5G) that did not express WT1 as the target cell. As used herein, C1498 is a mouse myelogenic leukemia cell line that does not express WT1.

Cytotoxic T cells (CTL) that kill C1498 (PM5G-mWT1) cells that are expressing WT1 but do not kill C1498 cells (PM5G) that are not expressing WT1 were induced.

Figure 17:
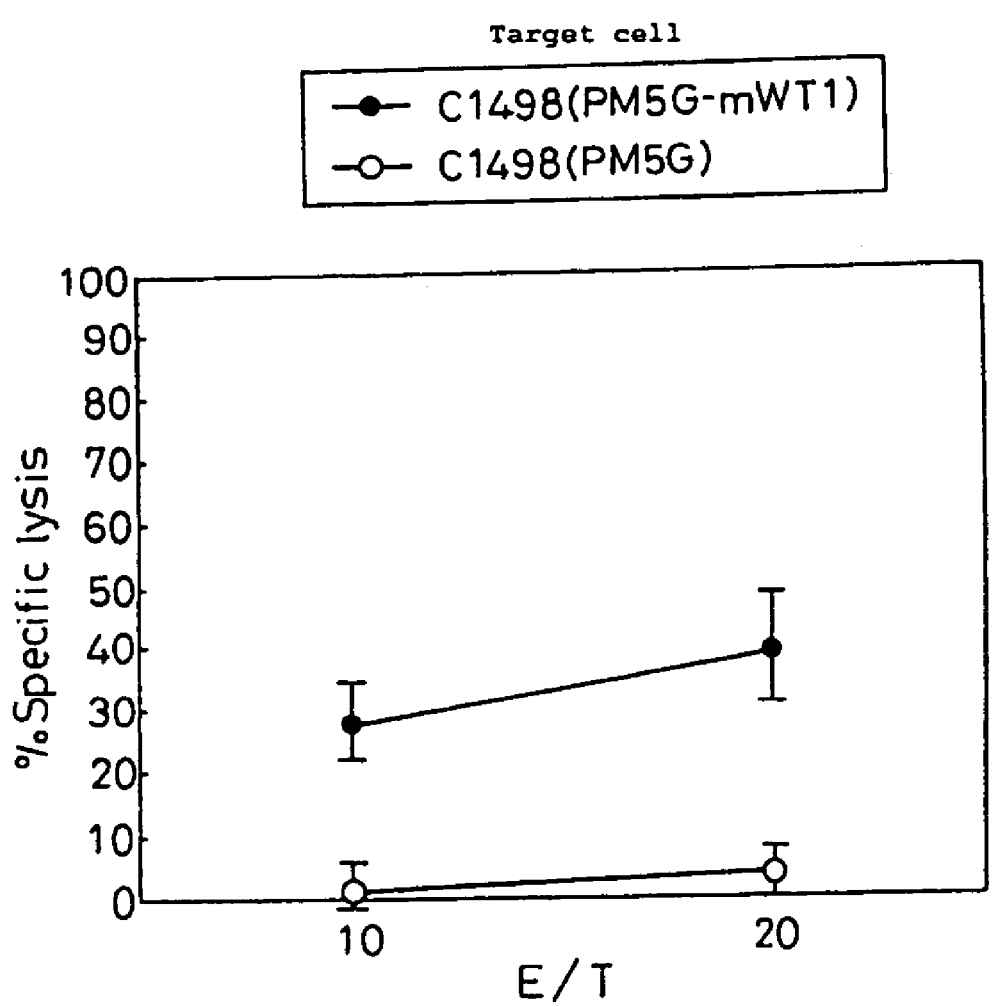
FIG. 17 is a graph showing the immunological effect when a plasmid expressing WT1 is administered to mice as a DNA vaccine.

The result is shown in FIG. 17.

As a control, a similar experiment as the above was performed in which plasmid that does not express WT1 (contain no WT1 cDNA) was intramuscularly injected to mice in stead of plasmid that expresses WT1. As in the above experiment, spleen cells were removed. After in vitro stimulation with C1498 (PM5G-mWT1) cells that express WT1, a killing assay was performed.

Figure 18:
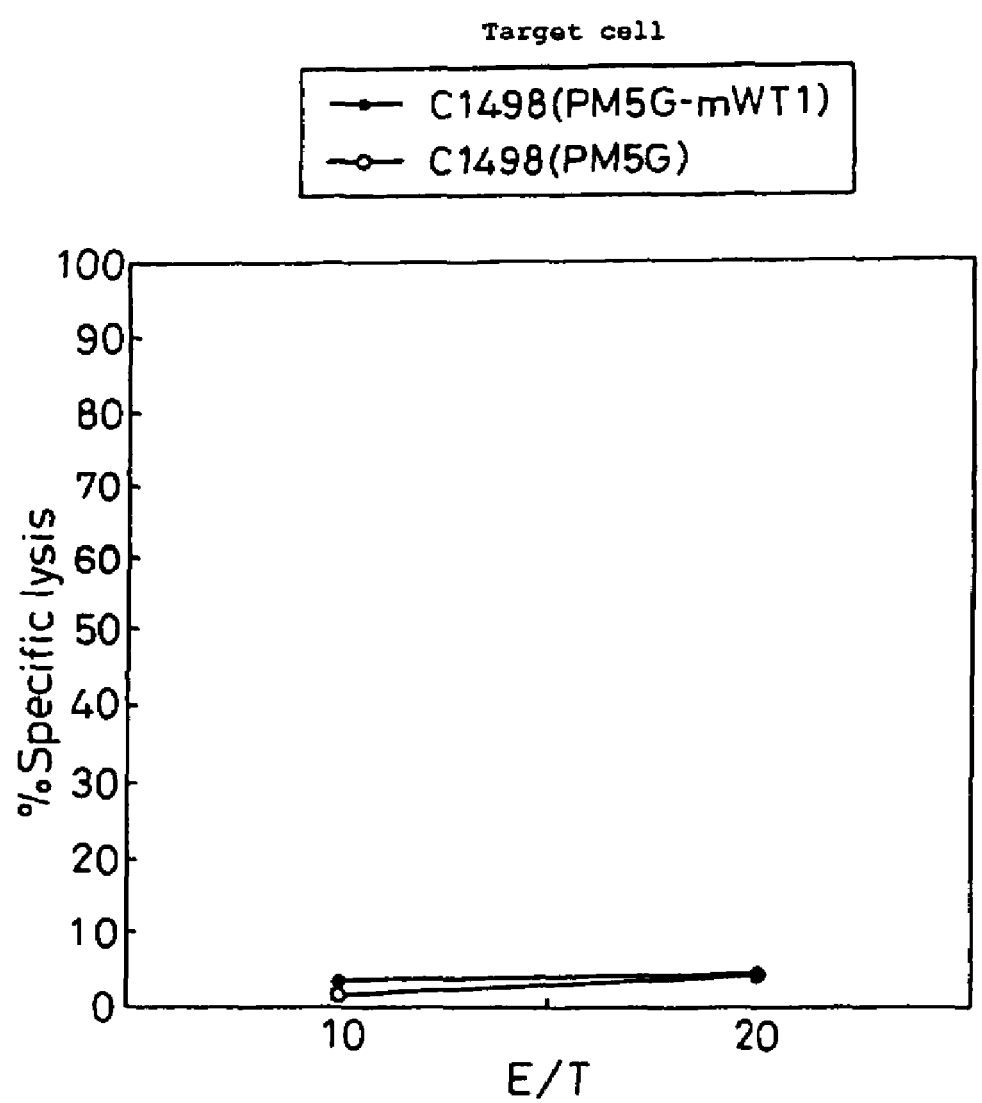
FIG. 18 is a graph showing the absence of the immunological effect when a plasmid not expressing WT1 is administered.

As shown in FIG. 18, no WT1-specific CTL was induced by intramuscular injection of the control plasmid DNA having no WT1 cDNA.

The above results demonstrated that the peptide of the present invention indeed functions as a tumor antigen and that it induced the growth of killer T cells (tumor cell-toxic T cells) against tumor cells. Therefore, the tumor antigen peptide of the present invention is useful as a cancer vaccine for leukemia and solid tumors that are accompanied by increased expression of the WT1 gene.

The invention claimed is:

1. An isolated polypeptide which consists of at most 12 contiguous amino acid residues of a human WT1 protein, wherein the polypeptide comprises SEQ ID NO: 7, binds to MHC proteins, and the polypeptide induces killer T cells when bound to MHC class I antigen.

2. The polypeptide of claim 1, which consists of SEQ ID NO: 7.

3. The polypeptide of claim 1, which binds to MHC class I antigen and MHC class II antigen.

4. A composition suitable for pharmaceutical use, comprising the polypeptide of claim 1 or claim 2 and a pharmaceutically acceptable carrier.

5. The composition of claim 4, wherein the pharmaceutically acceptable carrier is an adjuvant, surfactant, polyanion, or oil.

6. A method of inducing killer T cells against cancer, comprising administering an effective amount of the polypeptide of claim 1 to a patient.

7. The method of claim 6, wherein the cancer is accompanied by increased expression of the WT1 gene.

8. A method of inducing killer T cells against cancer, comprising administering an effective amount of the polypeptide of claim 2 to a patient.

9. The method of claim 8, wherein the cancer is accompanied by increased expression of the WT1 gene.

* * * * *

SEQUENCE LISTING

<160> NUMBER OF SEQ ID NOS: 8

<210> SEQ ID NO 1
<211> LENGTH: 449
<212> TYPE: PRT
<213> ORGANISM: Mus sp.

<400> SEQUENCE: 1

```
Met Gly Ser Asp Val Arg Asp Leu Asn Ala Leu Leu Pro Ala Val Ser
  1               5                  10                  15

Ser Leu Gly Gly Gly Gly Gly Cys Gly Leu Pro Val Ser Gly Ala
                 20                  25                  30

Arg Gln Trp Ala Pro Val Leu Asp Phe Ala Pro Pro Gly Ala Ser Ala
             35                  40                  45

Tyr Gly Ser Leu Gly Gly Pro Ala Pro Pro Ala Pro Pro Pro
         50                  55                  60

Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Leu His Phe
                 85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Thr Ile
        130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Gln His Ser Phe
                165                 170                 175

Lys His Glu Asp Pro Met Gly Gln Gln Gly Ser Leu Gly Glu Gln Gln
            180                 185                 190
```

-continued

```
Tyr Ser Val Pro Pro Val Tyr Gly Cys His Thr Pro Thr Asp Ser
        195                 200                 205
Cys Thr Gly Ser Gln Ala Leu Leu Arg Thr Pro Tyr Ser Ser Asp
    210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Met Ala Ala Gly Ser Ser Ser
                245                 250                 255
Ser Val Lys Trp Thr Glu Gly Gln Ser Asn His Gly Ile Gly Tyr Glu
            260                 265                 270
Ser Glu Asn His Thr Ala Pro Ile Leu Cys Gly Ala Gln Tyr Arg Ile
        275                 280                 285
His Thr His Gly Val Phe Arg Gly Ile Gln Asp Val Arg Arg Val Ser
    290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
        355                 360                 365
Gln Leu Lys Arg His Gln Arg Arg His Thr Gly Val Lys Pro Phe Gln
    370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp His Ser Cys Gln Lys Lys Phe Ala Arg Ser Asp Glu Leu Val
            420                 425                 430
Arg His His Asn Met His Gln Arg Asn Met Thr Lys Leu His Val Ala
        435                 440                 445
Leu

<210> SEQ ID NO 2
<211> LENGTH: 449
<212> TYPE: PRT
<213> ORGANISM: Homo sapiens

<400> SEQUENCE: 2

Met Gly Ser Asp Val Arg Asp Leu Asn Ala Leu Leu Pro Ala Val Pro
1               5                   10                  15
Ser Leu Gly Gly Gly Gly Gly Cys Ala Leu Pro Val Ser Gly Ala Ala
                20                  25                  30
Gln Trp Ala Pro Val Leu Asp Phe Ala Pro Gly Ala Ser Ala Tyr
            35                  40                  45
Gly Ser Leu Gly Gly Pro Ala Pro Pro Ala Pro Pro Pro Pro Pro
        50                  55                  60
Pro Pro Pro His Ser Phe Ile Lys Gln Glu Pro Ser Trp Gly Gly
65                  70                  75                  80
Ala Glu Pro His Glu Glu Gln Cys Leu Ser Ala Phe Thr Val His Phe
                85                  90                  95
Ser Gly Gln Phe Thr Gly Thr Ala Gly Ala Cys Arg Tyr Gly Pro Phe
            100                 105                 110
```

```
Gly Pro Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
        130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Gln His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Arg Thr Pro Tyr Ser Ser Asp
        210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
        370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Gly Ala Ser Ala Tyr Gly Ser Leu
  1               5
```

```
<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Cys Asn Lys Arg Tyr Phe Lys Leu
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Arg Met Phe Pro Asn Ala Pro Tyr Leu
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Tyr Ser Ser Asp Asn Leu Tyr Gln Met
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Cys Met Thr Trp Asn Gln Met Asn Leu
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Ser Leu Gly Glu Gln Gln Tyr Ser Val
  1               5
```